US012788893B2

(12) United States Patent
Groskopf et al.

(10) Patent No.: US 12,788,893 B2
(45) Date of Patent: Nov. 10, 2026

(54) MEDICAL INJECTION DEVICE WITH A RETAINED BIASING COMPONENT

(71) Applicant: Becton, Dickinson and Company, Franklin Lakes, NJ (US)

(72) Inventors: Roger Groskopf, Saddle Brook, NJ (US); Evan Leibowitz, Linden, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 774 days.

(21) Appl. No.: 18/027,698

(22) PCT Filed: Sep. 23, 2021

(86) PCT No.: PCT/US2021/051779
§ 371 (c)(1),
(2) Date: Mar. 22, 2023

(87) PCT Pub. No.: WO2022/066930
PCT Pub. Date: Mar. 31, 2022

(65) Prior Publication Data

US 2023/0381420 A1 Nov. 30, 2023

Related U.S. Application Data

(60) Provisional application No. 63/083,577, filed on Sep. 25, 2020.

(51) Int. Cl.
*A61M 5/315* (2006.01)
*A61M 5/24* (2006.01)

(52) U.S. Cl.
CPC .......... *A61M 5/31536* (2013.01); *A61M 5/24* (2013.01); *A61M 2005/2481* (2013.01)

(58) Field of Classification Search
CPC ................ A61M 5/31536; A61M 5/24; A61M 2005/2481; A61M 5/31525;
(Continued)

(56) References Cited

U.S. PATENT DOCUMENTS

| | | | |
|---|---|---|---|
| 9,421,334 B2 | 8/2016 | Quinn et al. | |
| 9,757,525 B2 * | 9/2017 | Cronenberg ...... | A61M 5/31535 |

(Continued)

FOREIGN PATENT DOCUMENTS

| | | | |
|---|---|---|---|
| CN | 107787234 A | 3/2018 | |
| WO | WO-9621482 A2 * | 7/1996 | ............ F41B 11/642 |
| WO | 2020016166 A1 | 1/2020 | |

*Primary Examiner* — Cris L. Rodriguez
(74) *Attorney, Agent, or Firm* — The Webb Law Firm

(57) ABSTRACT

A medical injection device including a housing having a distal end and a proximal end, a brake tower having a proximal end portion, a distal end portion, and a sidewall therebetween defining a longitudinal axis, and a cartridge received within the housing distally of the brake tower and holding a composition therein. The device further includes a retaining ring positioned between the proximal end portion of the cartridge and the distal end portion of the brake tower, wherein the retaining ring may be secured to an interior surface of the distal end portion of the brake tower. A spring washer component may also be provided, wherein the spring washer component may be retained by the retaining ring so as to bias the cartridge in a distal direction to prevent any movement of the cartridge during injection.

15 Claims, 11 Drawing Sheets

(58) Field of Classification Search

CPC .......... A61M 5/31535; A61M 5/31541; A61M 5/31551; A61M 5/31561; A61M 5/31585; A61M 2005/2407; A61M 5/31528; A61M 5/31573; A61M 5/3129; A61M 2005/2477; A61M 2005/3143; A61M 2005/2086; A61M 2005/2403; A61M 2005/2418

See application file for complete search history.

(56) References Cited

U.S. PATENT DOCUMENTS

| | | | | |
|---|---|---|---|---|
| 10,512,730 | B2 | 12/2019 | Bengtsson et al. | |
| 2003/0004466 | A1 | 1/2003 | Bitdinger et al. | |
| 2009/0275915 | A1* | 11/2009 | Harms .............. | A61M 5/31551 604/211 |
| 2011/0306939 | A1 | 12/2011 | Harms et al. | |
| 2014/0046268 | A1 | 2/2014 | Quinn et al. | |
| 2014/0094765 | A1 | 4/2014 | Pala | |
| 2015/0112274 | A1 | 4/2015 | Quinn et al. | |
| 2016/0193422 | A1* | 7/2016 | Cronenberg ...... | A61M 5/31543 604/211 |
| 2019/0022332 | A1* | 1/2019 | Kohlbrenner ..... | A61M 5/31561 |
| 2021/0260292 | A1 | 8/2021 | Plumptre et al. | |
| 2022/0088313 | A1* | 3/2022 | Jugl .................. | A61M 5/31553 |

* cited by examiner

MEDICAL INJECTION DEVICE WITH A RETAINED BIASING COMPONENT

CROSS-REFERENCE TO RELATED APPLICATIONS

This application is the United States national phase of International Patent Application No. PCT/US2021/051779 filed Sep. 23, 2021, and claims priority to United States Provisional Application Ser. No. 63/083,577, entitled "Medical Injection Device with a Retained Biasing Component", filed Sep. 25, 2020, the entire disclosures of which are hereby incorporated by reference in their entirety.

BACKGROUND OF THE INVENTION

Field of the Invention

The present disclosure relates generally to components useful as replacements for helical coil springs for medical devices, and, in particular embodiments or aspects, to injection devices including a brake tower having a biasing component such as, e.g., a spring washer component and/or a retaining ring.

Description of Related Art

Medical injection devices often utilize resilient members, such as springs, placed between various components, to bias the components in order to ensure more accurate drug delivery. However, there are shortcomings to the use of current resilient members used in medical injection devices, such as a lack of control and load recovery. Accordingly, there is a need in the art for a more robust component to allow for greater load recovery.

SUMMARY OF THE INVENTION

Provided herein is a medical injection device including a housing having a distal end and a proximal end, a brake tower having a proximal end portion, a distal end portion, and a sidewall therebetween defining a longitudinal axis, a cartridge received within the housing distally of the brake tower and holding a composition therein, where a proximal end portion of the cartridge is configured to extend at least partially within the distal end portion of the brake tower along the longitudinal axis, and a retaining ring positioned between the proximal end portion of the cartridge and the distal end portion of the brake tower.

The device may further include a spring washer component, where the spring washer component is held within the distal end portion of the brake tower by the retaining ring, and where the retaining ring is secured to an interior surface of the distal end portion of the brake tower. The spring washer component may be configured to bias the cartridge distally relative to the brake tower. The spring washer component and the retaining ring may each have an opening formed therethrough, and where the respective openings are sized to allow a piston rod to extend therethrough. The spring washer component may be a sinusoidal spring washer. The retaining ring may be a C-shaped ring. The retaining ring may be secured within a groove formed within an interior sidewall surface of the brake tower. The retaining ring may include a plurality of projections extending therefrom. The retaining ring is substantially convex.

The device may further include a spring washer component, with the spring washer component held against the distal end portion of the brake tower by the retaining ring.

In a further aspect or embodiment, a medical injection device includes a housing having a distal end and a proximal end, a brake tower having a proximal end portion, a distal end portion, and a sidewall therebetween defining a longitudinal axis, a cartridge received within the housing distally of the brake tower and holding a composition therein, where a proximal end portion of the cartridge is configured to extend at least partially within the distal end portion of the brake tower along the longitudinal axis, a cartridge housing received within the housing distally of the brake member and configured to hold the cartridge therein, an injection needle at a distal end of the housing and in fluid communication with the cartridge, an actuation member at a proximal end of the housing, the actuation member configured to actuate the medical injection device to deliver the composition through the injection needle, a spring washer component, wherein the spring washer component is positioned within the distal end portion of the brake tower, and a retaining ring positioned between the proximal end portion of the cartridge and the distal end portion of the brake tower, where the retaining ring is secured to an interior surface of the distal end portion of the brake tower to hold the spring washer component within the distal end portion of the brake tower.

The spring washer component may be configured to bias the cartridge distally relative to the brake tower. The spring washer component and the retaining ring may each have an opening formed therethrough, and where the respective openings are sized to allow a piston rod to extend therethrough. The spring washer component may be a sinusoidal spring washer. The retaining ring may be a C-shaped ring.

In a further aspect or embodiment, a medical injection device includes a housing having a distal end and a proximal end, a brake tower having a proximal end portion, a distal end portion, and a sidewall therebetween defining a longitudinal axis, a cartridge received within the housing distally of the brake tower and holding a composition therein, wherein a proximal end portion of the cartridge is configured to extend at least partially within the distal end portion of the brake tower along the longitudinal axis, a cartridge housing received within the housing distally of the brake member and configured to hold the cartridge therein, an injection needle at a distal end of the housing and in fluid communication with the cartridge, an actuation member at a proximal end of the housing, the actuation member configured to actuate the medical injection device to deliver the composition through the injection needle, and a retaining ring positioned between the proximal end portion of the cartridge and the distal end portion of the brake tower, where the retaining ring is press-fittingly secured to an interior surface of the distal end portion of the brake tower.

The retaining ring may include a plurality of projections extending therefrom. The retaining ring may be substantially convex.

DESCRIPTION OF THE INVENTION

Figure 1:
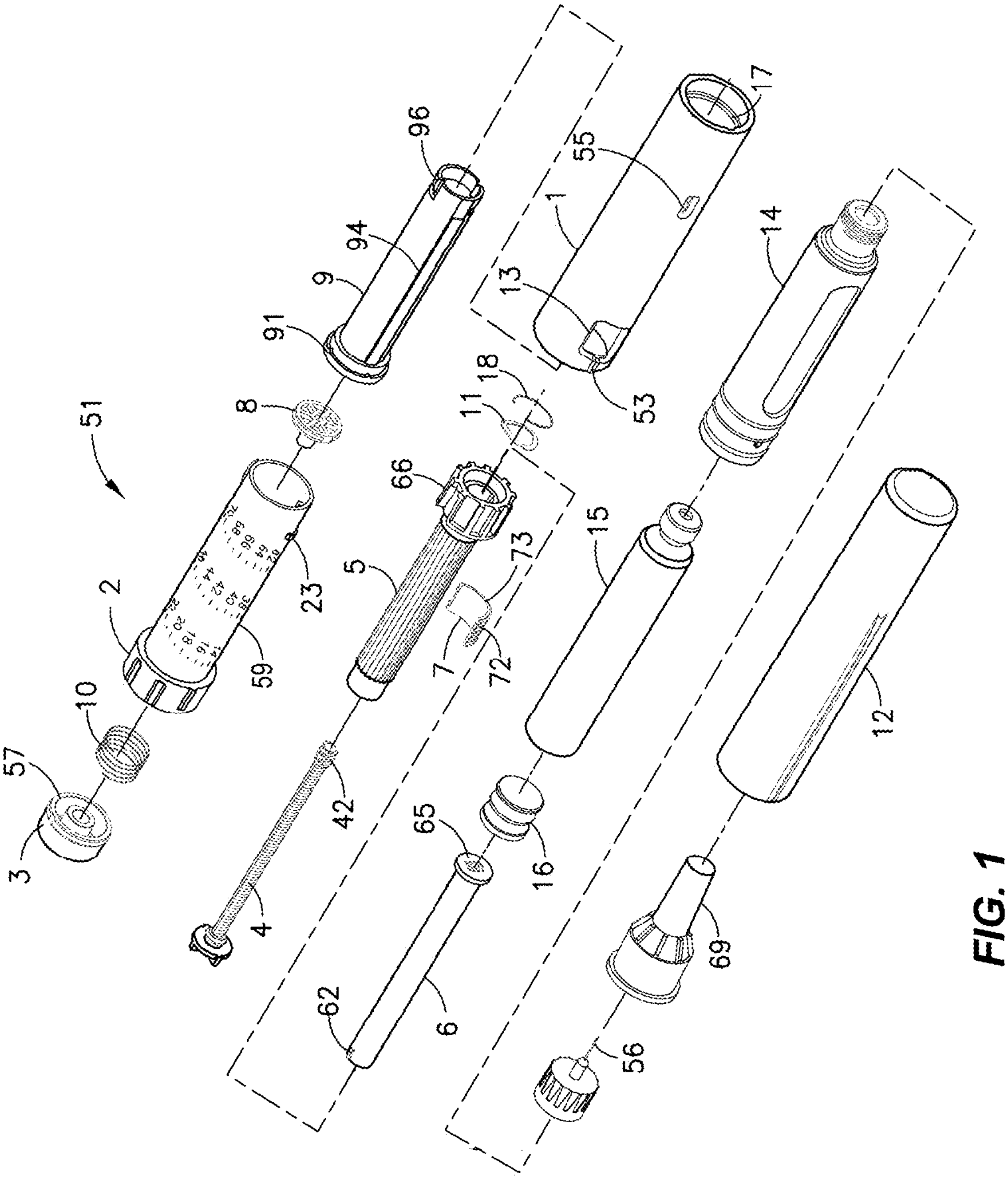
FIG. 1 is an exploded view of a medical injection device with a brake tower, spring washer component, and retaining ring according to a non-limiting embodiment or aspect as described herein.

The use of numerical values in the various ranges specified in this application, unless expressly indicated otherwise, are stated as approximations as though the minimum and maximum values within the stated ranges are both preceded by the word "about". As used herein, the term "about" means the stated value ±10%. In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

Provided herein is a brake tower with a biasing component for use as a replacement for a spring in a medical device.

Figure 11:
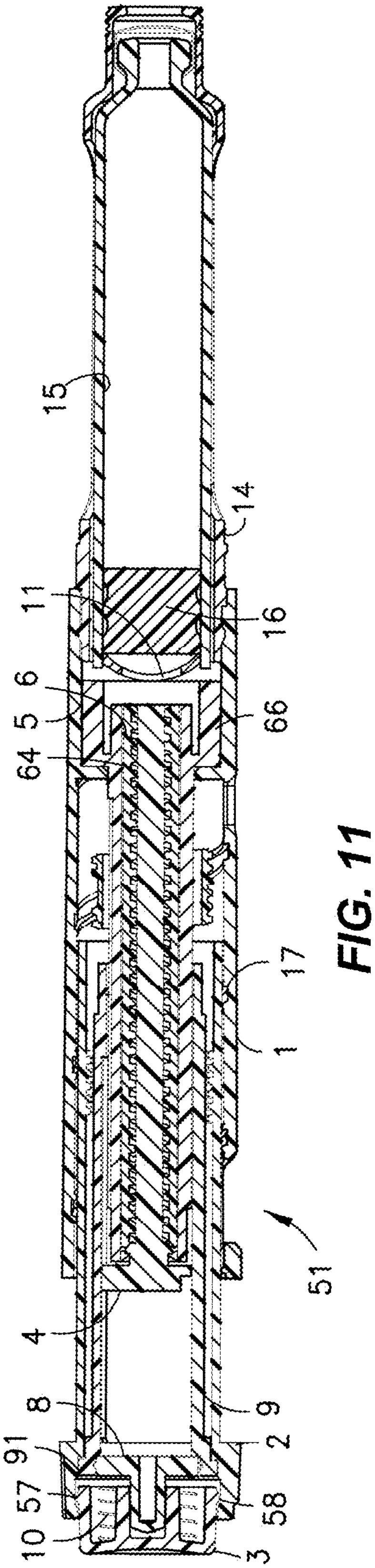
FIG. 11 is a cross-sectional view of a medical injection device including a brake tower with a retaining ring according to a non-limiting embodiment or aspect as described herein.

Referring to FIG. 1 and FIG. 11, a medical injection device in accordance with an aspect of the present disclosure is shown. Such devices, such as injection pens, are described in U.S. Pat. No. 9,421,334, which is incorporated herein by reference in its entirety. With reference to FIGS. 1 and 11, shown are an exploded (FIG. 1) and cross-sectional (FIG. 11) view of an injection pen 51 for delivery of a composition to a user. As shown, injection pen 51 includes a pen upper body or housing 1, which houses a plurality of dose setting and injection components. Pen upper body 1 is connected to a cartridge housing 14, which houses cartridge 15. Injection pen 51 can also include a lower pen cap 12 to cover the cartridge 15 and cartridge housing 14 when injection pen 51 is not in use. As shown, injection pen 51 can include a dose set knob 2 that includes a knob-like portion that is rotated by a user to set a desired dose. Dose set knob 2 can also include a plurality of numerals, corresponding to a number of dosage units that is visible through a window 13 provided on pen upper body 1. A user rotates dose set knob 2 until the desired dose is visible in window 13. Pen upper body 1 can include an arrow or other indicator 53 to precisely indicate the set dose. Once the desired dose is set, a user presses a button 3 until the set dosage amount is completely injected. An outer shield 69 can cover a needle 56 to prevent accidental needle sticks upon removal of the lower pen cap 12.

Injection pen 51 can include push button 3, provided at a proximal end, closest to a user and farthest from needle 56, of pen upper body 1. Push button 3 can include an annular bead or rim 57 that engages with a corresponding annular groove (not shown) provided on the internal surface of dose set knob 2. The annular rim and groove connection can be a friction fit that maintains push button 3 in a biased position on dose set knob 2 under the force of a button spring 10, but allows push button 3 to be pushed into dose set knob 2 for injecting a set dose. The interior of push button 3 can accommodate a setback bearing insert 8 that rests on an internal surface at a proximal end of a setback member or driver 9. Push button 3 can be designed to rotate freely on setback bearing insert 8.

Setback member or driver 9 can be a cylindrical member, coaxial with and surrounded by dose set knob 2. Setback member 9 can be provided co-axially around a brake tower 5. Brake tower 5 can be axially and rotatably fixed to pen upper body 1. In non-limiting embodiments or aspects, brake tower 5 co-axially surrounds a piston rod 6. Piston rod 6 can include a set of keys (not shown) that engage a slot (not shown) internal to brake tower 5 to rotatably lock piston rod 6 to brake tower 5. Piston rod 6 can include a plurality of threads (not shown) provided on the interior surface thereof. Piston rod 6 can co-axially surround a lead screw 4 that includes a series of threads 42 at least at its distal end. Lead screw threads 42 can be configured to be in threaded engagement with the internal threads (not shown) provided on the interior of piston rod 6. Due to its threaded engagement with lead screw 4, piston rod 6 can be moved into cartridge 15 during injection to press on a stopper 16 provided inside cartridge 15 to expel a dose of medication.

Following assembly, and when injection pen 51 is ready to be used, a dose for drug delivery can be set. To set a dose using injection pen 51 as described herein, a user rotates the knob portion of dose set knob 2 relative to pen upper body 1. An outer surface 59 of the dose set knob 2 can include a thread 23, which is in threaded engagement with a plurality of threads 17 provided on the internal surface of the pen upper body 1, as shown in FIGS. 1 and 11. Accordingly, as dose set knob 2 is rotated relative to pen upper body 1, dose set knob 2 screws or advances a distance out of pen upper body 1, as shown in FIG. 11. Dose set knob 2 can include an annular shoulder or rim on the interior surface thereof near the proximal end. This annular shoulder can engage with an enlarged portion or head 91 of setback member 9, as shown in FIG. 11. The annular shoulder of dose set knob 2 can include a series of teeth or ridges that engage with a plurality of similarly shaped teeth or ridges (not shown) provided on enlarged head 91 of setback member 9. Dose set knob teeth and setback member teeth can extend in opposite axial directions. During dose setting, dose set knob 2 can be free to rotate with respect to setback member 9 in both clockwise and counter-clockwise directions. As this occurs, the plurality of teeth or ridges on dose set knob 2 can slip past the teeth provided on head portion 91 of setback member 9, thus providing a tactile signal or clicking noise to indicate the setting of a dosage amount.

With regard to the injection mechanism, as described above, lead screw 4 can include a plurality of threads 42 at its distal end that are in threaded engagement with a plurality of threads 64 that can be provided along the entire length of a hollow piston rod 6 as shown in FIG. 1. Piston rod 6 can be held non-rotatably with respect to pen upper body 1 due to a non-rotatable coupling with brake tower 5, which can be held axially and rotatably fixed with respect to the pen upper body 1. Piston rod 6 can include a key or set of keys 62 at its distal end that engage with a slot (not shown) provided on the internal surface of the brake tower 5 to prevent relative rotation therebetween while permitting piston rod 6 to move axially with respect thereto. Threads 42 of lead screw 4 can include a flat portion (not shown) corresponding to a flat portion 65 of piston rod 6, such that axial movement of the lead screw during dose setting does not result in axial movement of the piston rod 6. Accordingly, rotation of lead screw 4 during injection of a dose can cause the threads 42 of lead screw 4 to engage threads 64 of the piston rod 6, thereby axially moving piston rod 6. Because piston rod 6 can be non-rotatable with respect to body 1, as lead screw 4 is caused to rotate during injection, as described above due to its rotational coupling setback member 9, piston rod 6 through its threaded engagement with lead screw 4 can be caused to move in the distal direction to press against stopper 16 provided in cartridge 15, thus expelling a liquid medication therefrom.

With reference to the present disclosure, injection pen 51 includes brake tower 5 and cartridge 15, as described above. In previous injections pens, such as that which is described in U.S. Pat. No. 9,421,334, a wave clip (or wave spring) has been provided between a distal end of the brake tower 5 and the cartridge 15 so as to bias the cartridge 15 in a distal direction to prevent any movement of the cartridge 15 during injection, thereby ensuring that an accurate dose is injected. However, the use of a wave clip alone has shortcomings such as, e.g., lack of control and load recovery. Thus, in accordance with an aspect of the present disclosure, and as is shown in FIG. 1, injection pen 51 includes both a spring washer component 11 and a retaining ring 18 to achieve the biasing of cartridge 15 with respect to brake tower 5. As will be described in further detail below with respect to FIGS. 2-4, the retaining ring 18 is held in contact within the brake tower 5, thereby holding the spring washer component 11 in place relative to the brake tower 5 to provide for, e.g., better control and load recovery.

Figure 2:
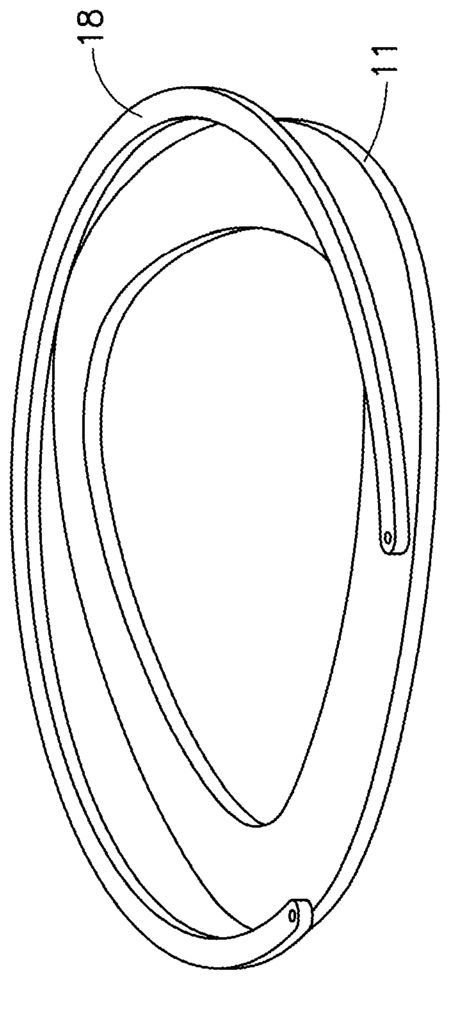
FIG. 2 is a perspective view of a spring washer component and retaining ring for use with a brake tower according to a non-limiting embodiment or aspect as described herein.

Referring to FIG. 2, shown is a non-limiting embodiment of the spring washer component 11 and retaining ring 18 for a medical injection device. The spring washer component 11 may be any appropriate resilient member such as, e.g., a sinusoidal spring washer, etc. The spring washer component 11 may be formed of any appropriate material such as, e.g., a metal or metal alloy, a polymeric material, a thermoplastic, etc.

A retaining ring 18 may also be provided. As shown in FIG. 2, retaining ring 18 may be formed as, e.g., a C-shaped ring. However, it is to be understood that retaining ring 18 may be any appropriate shape such as, e.g., a circular ring, a U-shaped ring, etc. Furthermore, retaining ring 18 may be formed of more than one component (e.g., two U-shaped components). The retaining ring 18 may be formed of any appropriate material such as, e.g., a metal or metal alloy, a polymeric material, a thermoplastic, etc.

Figure 3:
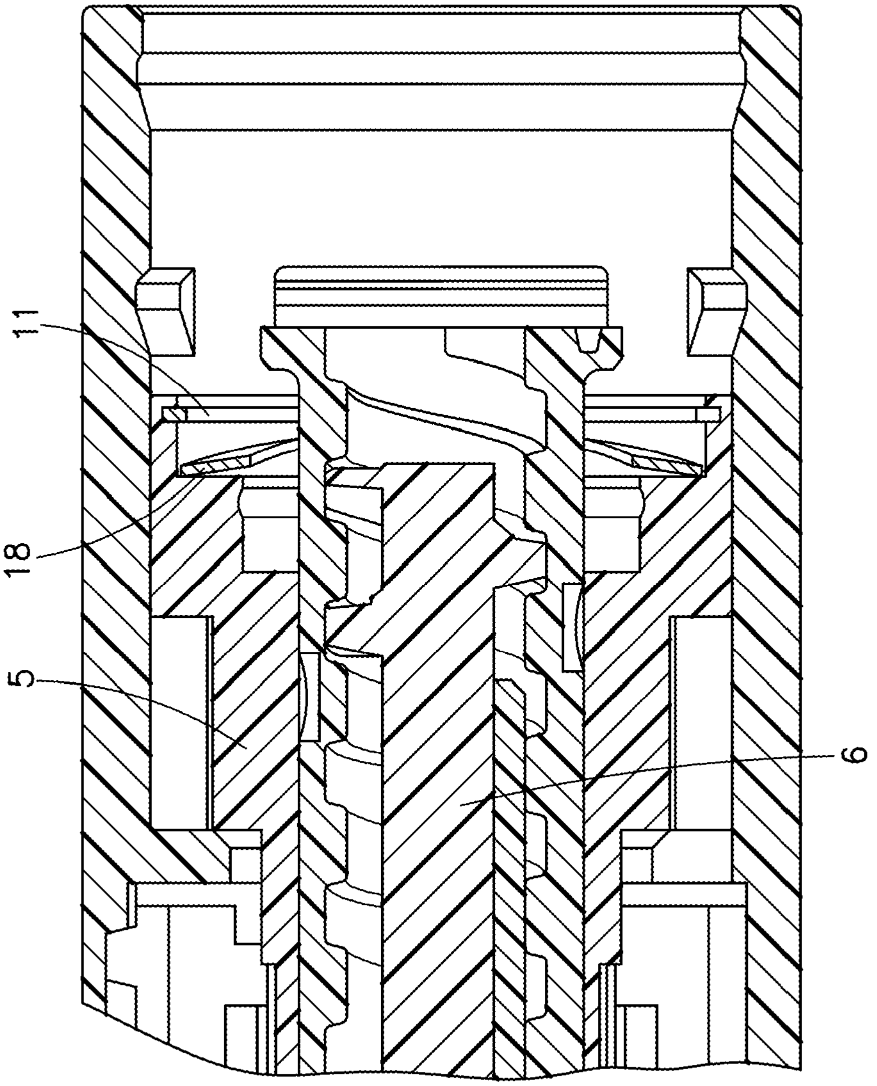
FIG. 3 is a cross-sectional view of a medical injection device with a brake tower, spring component, and retaining ring according to a non-limiting embodiment or aspect as described herein, showing a pre-engagement position.
Figure 4:
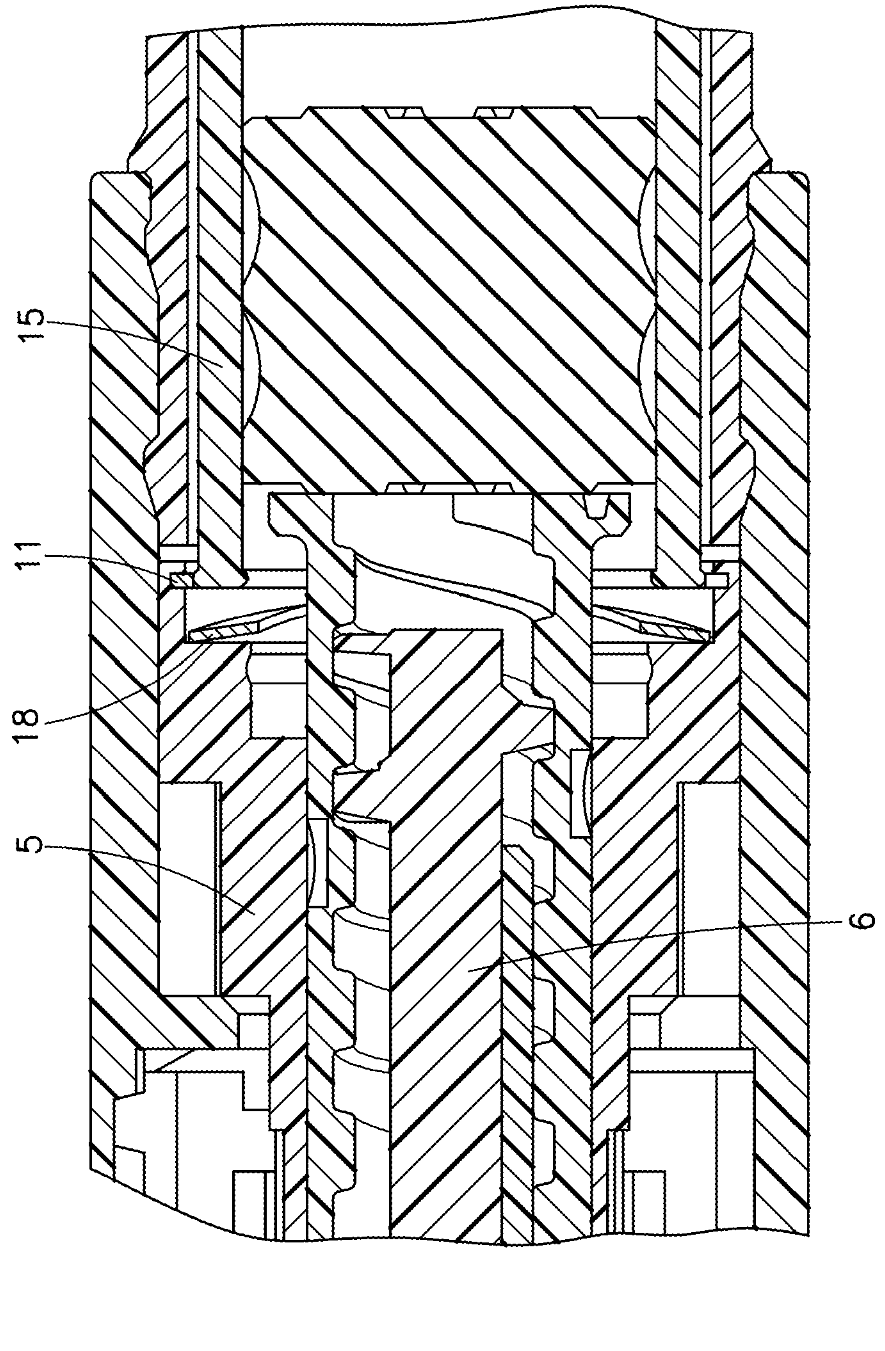
FIG. 4 is a cross-sectional view of a medical injection device with a brake tower, spring component, and retaining ring according to a non-limiting embodiment or aspect as described herein, showing an engagement position.

Referring to FIGS. 3 and 4, a non-limiting embodiment or aspect of an interface between a brake tower 5 and cartridge 15 for a medical injection device is shown in a pre-engagement position (FIG. 3) prior to assembly and insertion of cartridge 15 and an engagement position (FIG. 4) after insertion of cartridge 15. A brake tower can assume any useful configuration for use in a medical injection device. In non-limiting embodiments or aspects, brake tower 5 is cylindrical, and has a proximal end, a distal end, and a sidewall therebetween defining a longitudinal axis. In non-limiting embodiments or aspects, brake tower 5 is at least partially hollow, and the proximal end, distal end, and sidewall define an at least partially open interior that can receive one or more other components of a medical injection device. For example, a piston rod 6 may extend at least partially through the interior of the brake tower 5.

In non-limiting embodiments or aspects, the distal end portion of brake tower 5 is enlarged, e.g., by having a greater circumference than the proximal end. In non-limiting embodiments or aspects, distal end of brake tower 5 is configured to partially receive a proximal end of cartridge 15, as is shown in FIG. 3. As described above, the spring washer component 11 is positioned within the interior of the distal end of the brake tower 5 between the proximal end of the cartridge 15 and an interior shoulder surface the brake tower 5 so as to bias the cartridge 15 in a distal direction to prevent any movement of the cartridge 15 during injection.

Furthermore, the retaining ring 18 is also positioned within the interior of the distal end portion of the brake tower 5, with the retaining ring 18 acting to hold the spring washer component 11 within the distal end portion of the brake tower 5. The retaining ring 18 may be coupled to the interior surface of the distal end portion of brake tower 5 by any appropriate method or means. For example, a slot or groove may be formed within the interior sidewall of the distal end portion of brake tower 5, with the retaining ring 18 held within the slot or groove by way of an interference fit. Additionally and/or alternatively, the retaining ring 18 may be held on or within the inner surface of the distal end portion of brake tower 5 by way of, e.g., an adhesive, one or more fasteners, etc.

Referring again to FIGS. 3 and 4, the retaining ring 18 is positioned a predetermined distance from the distal end of brake tower 5 so as to effectively retain the spring washer component 11 within the brake tower 5. However, it is to be understood that the position of retaining ring 18 may be altered based upon, e.g., the size and/or type of spring washer component 11.

As is also shown in FIG. 4, the spring washer component 11 and retaining ring 18 cooperate to bias the cartridge 15 with respect to the brake tower 5, yet allow the piston rod 6 to pass therethrough.

Figure 5:
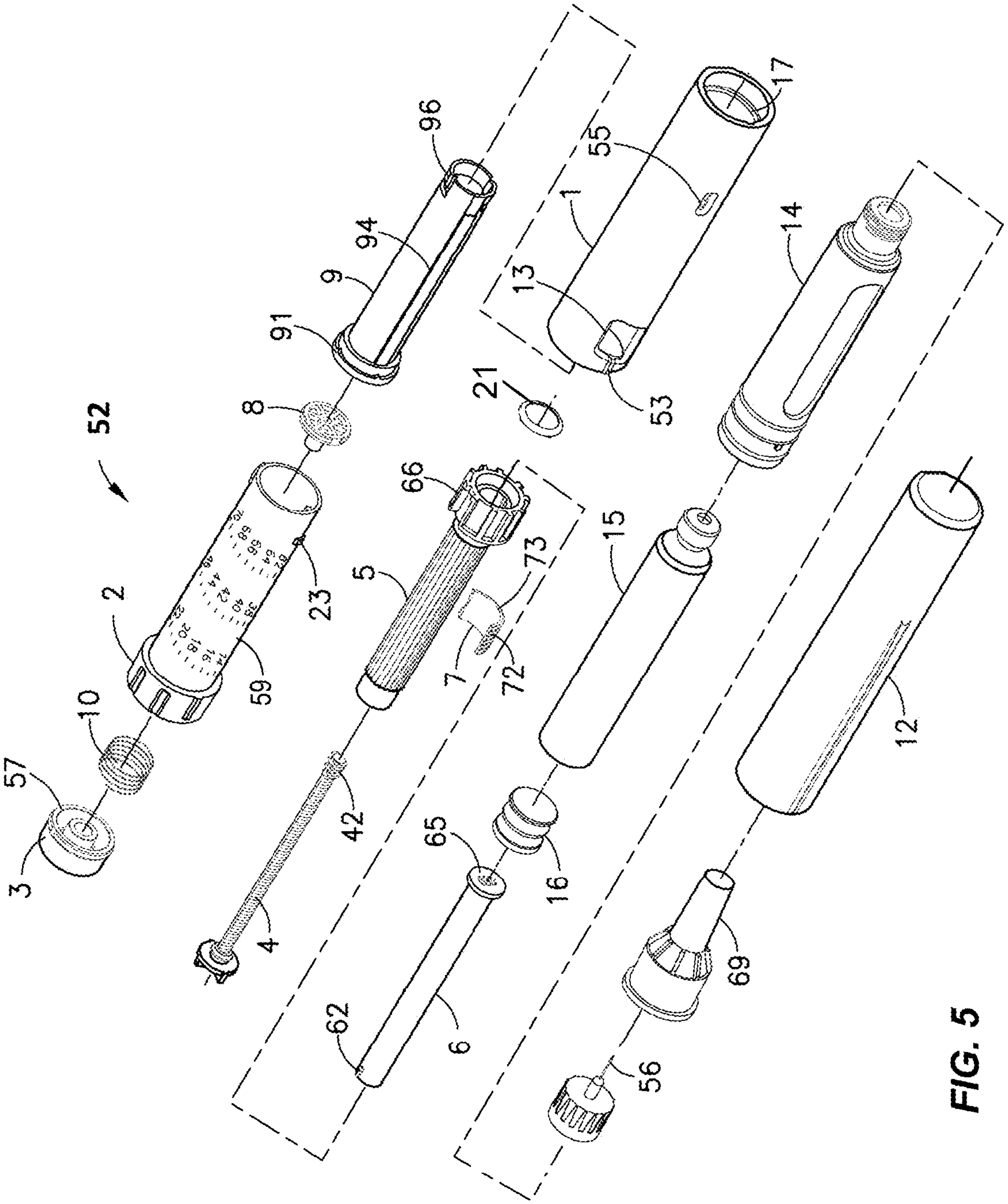
FIG. 5 is an exploded view of a medical injection device including a brake tower with a retaining ring according to another non-limiting embodiment or aspect as described herein.

Next, referring to FIG. 5, a medical injection device in accordance with another aspect of the present disclosure is shown. Specifically, an exploded view of an injection pen 52 is shown in FIG. 5. As is evidenced by the common reference numerals, the overall construction of injection pen 52 is substantially similar to injection pen 51 shown and described with respect to FIGS. 1 and 11. Thus, the common components (and their functions) between injection pen 51 and injection pen 52 will not be reiterated herein.

However, unlike injection pen 51 described above, which utilizes both a spring washer component 11 and retaining ring 18 to bias the cartridge 15 with respect to the brake tower 5, injection pen 52 shown in FIG. 5 utilizes only a pressed retaining ring 21 to achieve this function.

Figure 6:
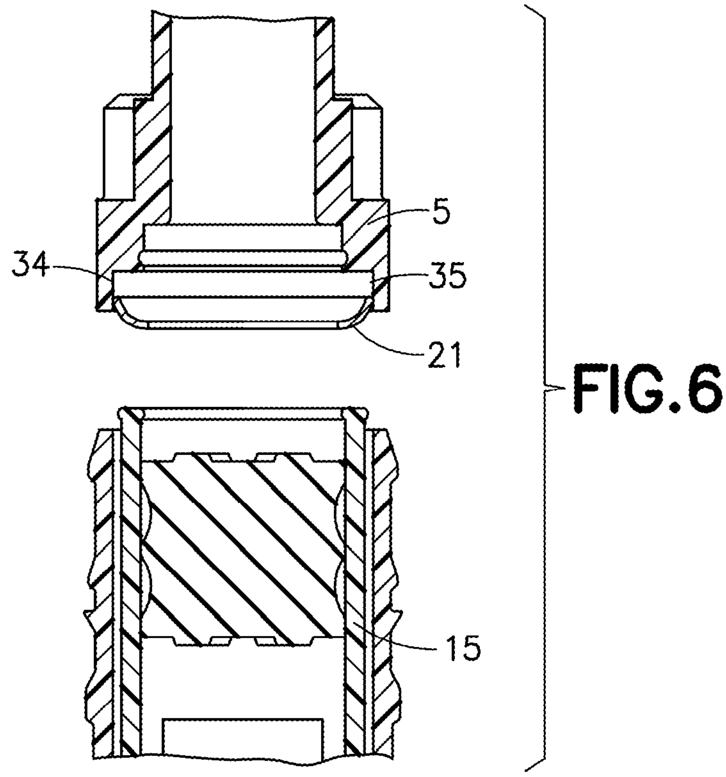
FIG. 6 is a cross-sectional view of a medical injection device with a brake tower and retaining ring according to a non-limiting embodiment or aspect as described herein.
Figure 7:
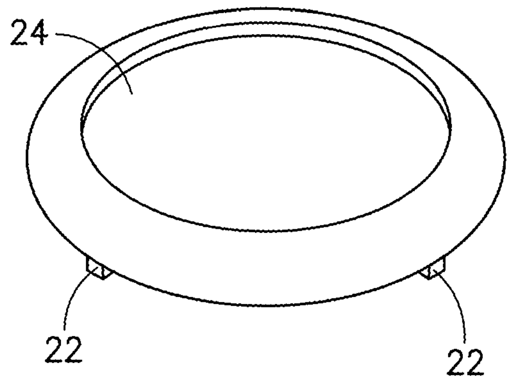
FIG. 7 is a perspective view of a retaining ring for use with a brake tower according to a non-limiting embodiment or aspect as described herein.
Figure 8:
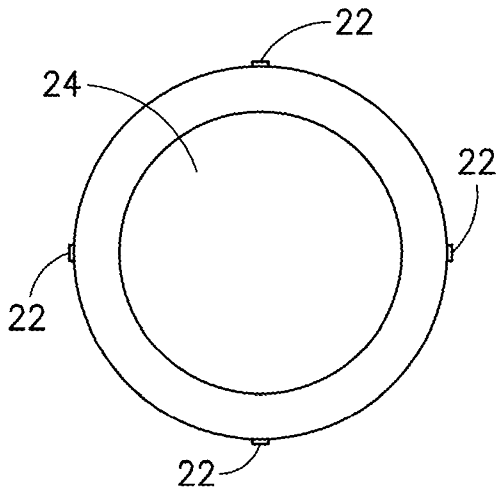
FIG. 8 is a top view of a retaining ring for use with a brake tower according to a non-limiting embodiment or aspect as described herein.
Figure 9:
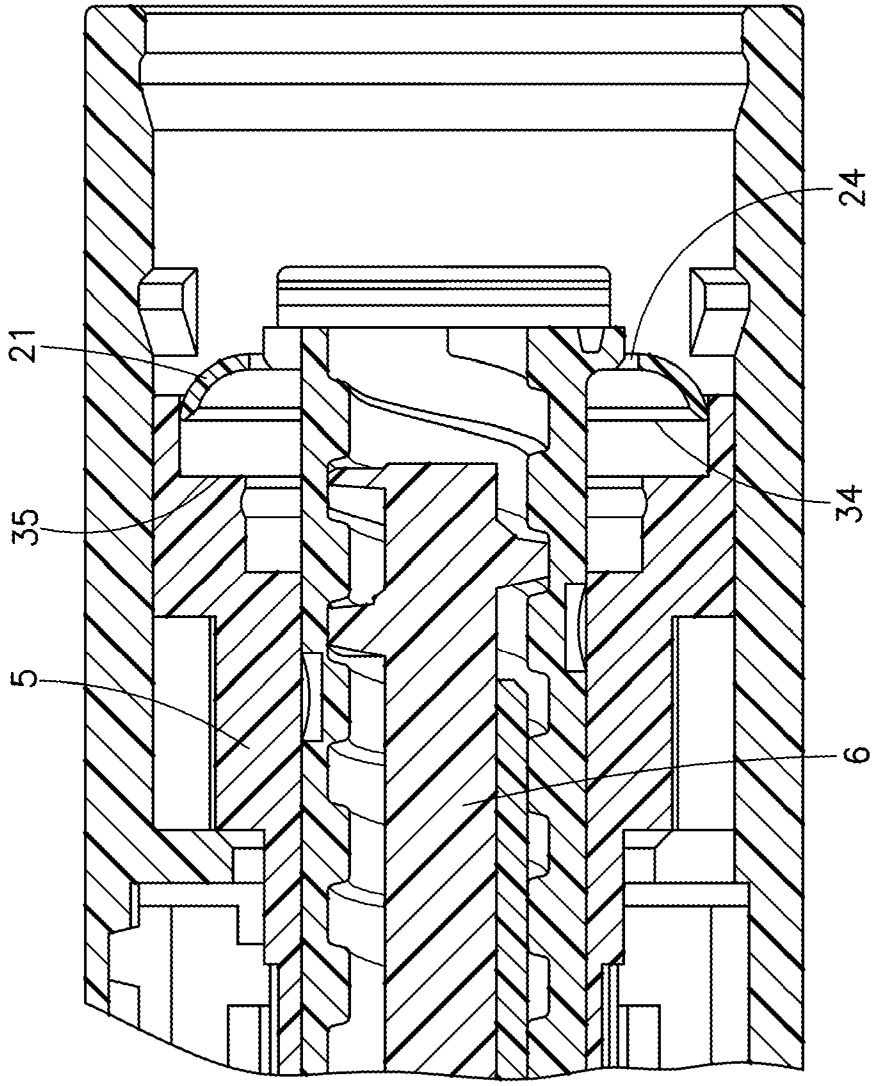
FIG. 9 is a cross-sectional view of a medical injection device with a brake tower and retaining ring according to a non-limiting embodiment or aspect as described herein, showing a pre-engagement position.
Figure 10:
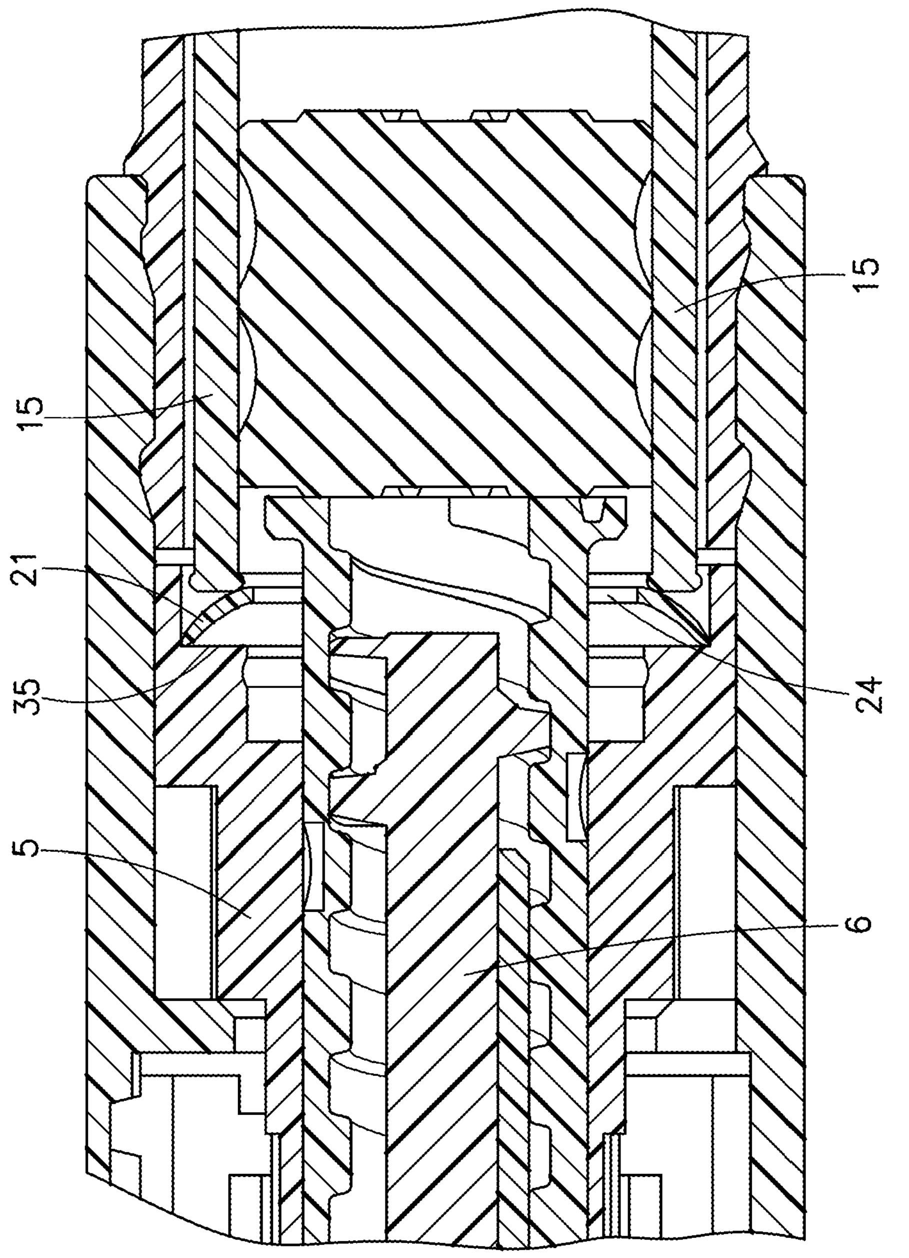
FIG. 10 is a cross-sectional view of a medical injection device with a brake tower and retaining ring according to a non-limiting embodiment or aspect as described herein, showing an engagement position.

Referring to FIGS. 6-10, prior to final assembly of the injection pen 52, the pressed retaining ring 21 is positioned within the interior of the distal end portion of the brake tower 5, as shown in FIGS. 6 and 9. Specifically, the pressed retaining ring 21 is initially held within a snap groove 34 formed within the interior surface of the distal end portion of brake tower 5. Then, when the proximal end of cartridge 15 is inserted into the distal end of brake tower 5 during assembly of injection pen 52, as shown in FIG. 10, the pressed retaining ring 21 is shifted within the distal end portion of brake tower 5 until reaching a final position 35 within the distal end portion of brake tower 5. In one aspect or embodiment, the final position 35 is defined by a stop within brake tower 5.

Similar to spring washer component 11 described above, when pressed retaining ring 21 is in the final position 35, pressed retaining ring 21 functions to bias the cartridge 15 in a distal direction to prevent any movement of the cartridge 15 during injection.

Referring to FIGS. 7 and 8, in accordance with one embodiment or aspect of the present disclosure, pressed retaining ring 21 is shown in more detail. Specifically, pressed retaining ring 21 is substantially convex in shape, with a central opening 24 formed therein, although other suitable shapes may be utilized. The substantially convex shape of pressed retaining ring 21 provides for spring-like properties, thereby enabling the pressed retaining ring 21 to bias the cartridge 15 in the distal direction.

As shown in FIG. 10, the central opening 24 is sized so as to permit the piston rod 6 to travel therethrough.

The pressed retaining ring 21 further includes a plurality of projections 22. As shown in FIG. 8, four projections 22 may be utilized. However, it is to be understood that more or fewer projections 22 are possible. The projections 22 are configured to provide a piercing or similar interface between the pressed retaining ring 21 and the final position 35 on the interior surface of the brake tower 5 such that the pressed retaining ring 21 is substantially secured at the final position 35.

The pressed retaining ring 21 may be formed of any appropriate material such as, e.g., a metal or metal alloy, a polymeric material, a thermoplastic, etc.

Additionally and/or alternatively, the pressed retaining ring 21 may be held at the final position 35 of the distal end portion of brake tower 5 by way of, e.g., an adhesive, one or more fasteners, etc.

Figure 12:
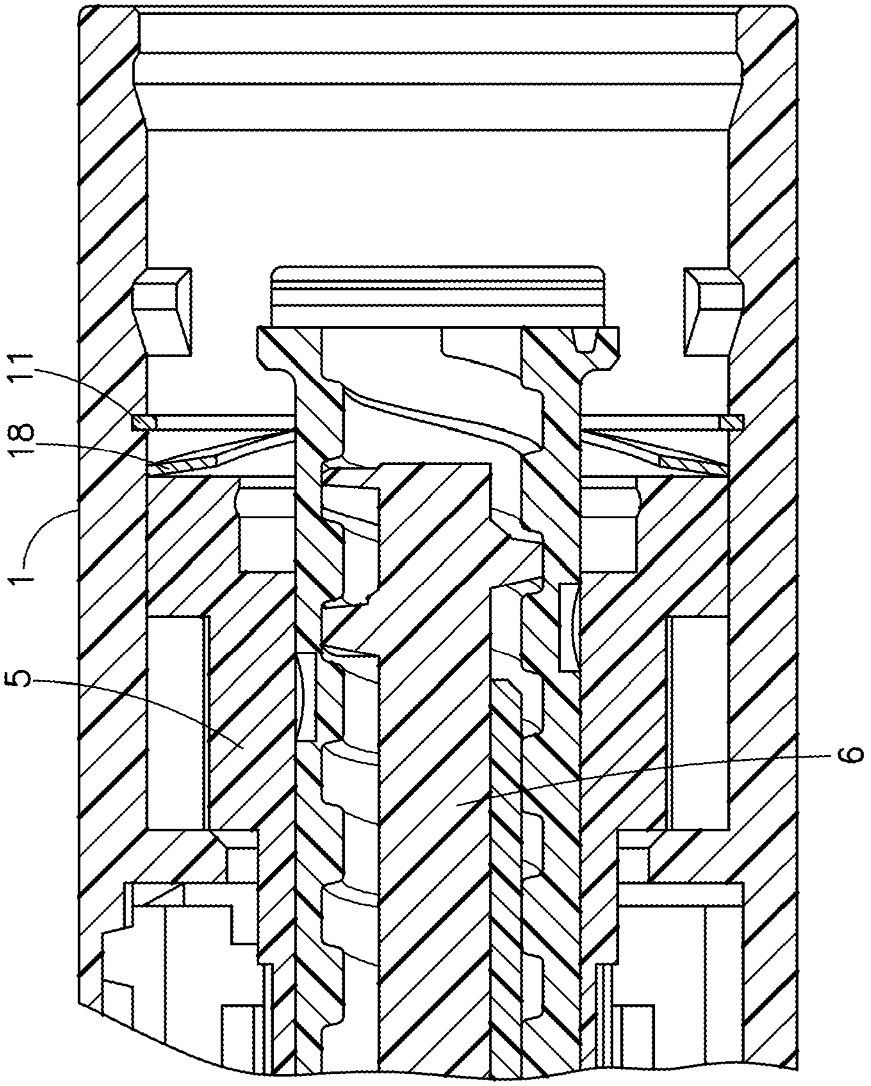
FIG. 12 is a cross-sectional view of a medical injection device with a brake tower, spring component, and retaining ring according to a further non-limiting embodiment or aspect as described herein, showing a pre-engagement position.
Figure 13:
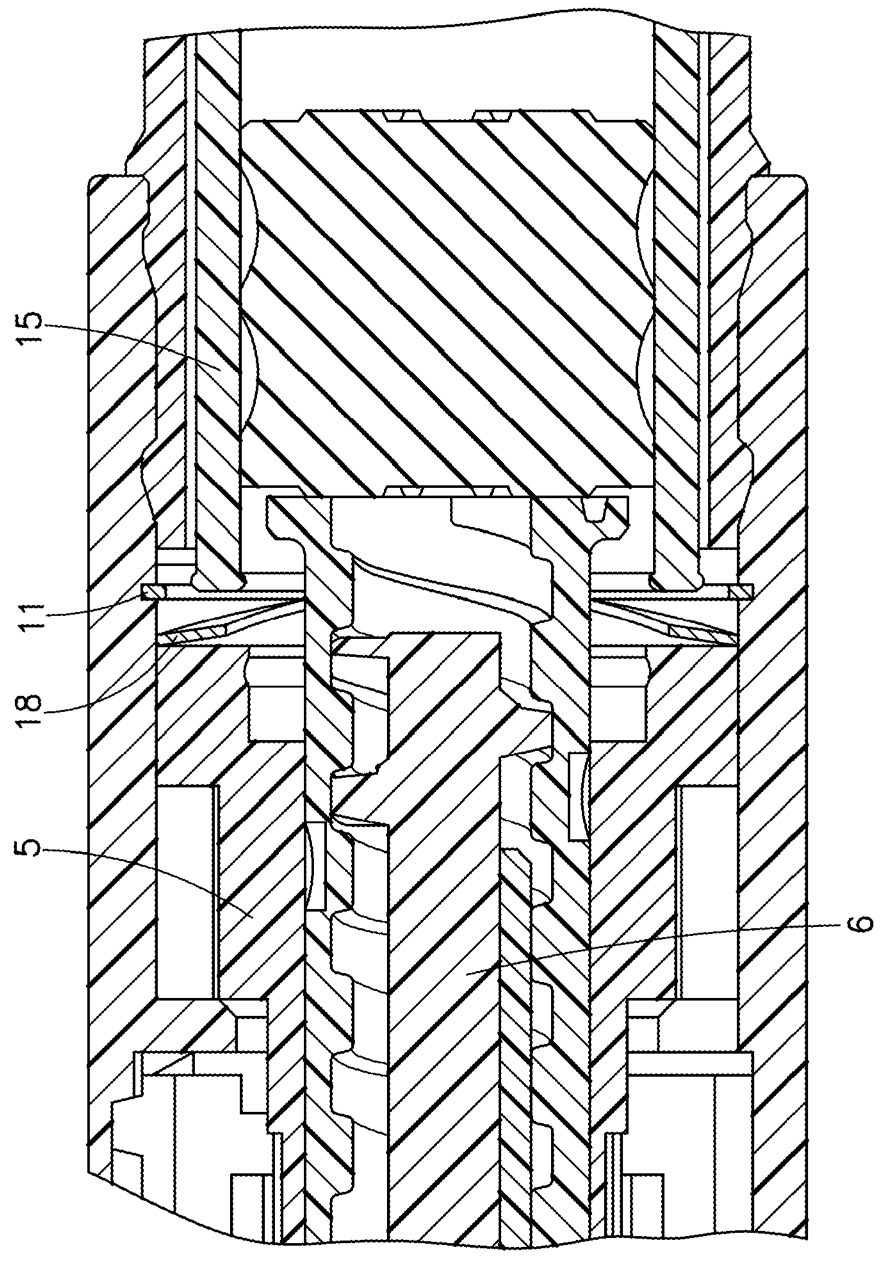
FIG. 13 is a cross-sectional view of a medical injection device with a brake tower, spring component, and retaining ring according to a further non-limiting embodiment or aspect as described herein, showing an engagement position.

Referring to FIGS. 12 and 13, in a further non-limiting embodiment or aspect, the spring washer component 11 is positioned against the distal end of the brake tower 5 rather than being positioned within the interior of the distal end of the brake tower 5 as shown in FIGS. 3 and 4. Further, as shown in FIGS. 12 and 13, the retaining ring 18 is engaged with the housing 1 to hold the spring washer component 11 against the distal end of the brake tower 5. The retaining ring 18 may be received within a groove defined by the housing 1. The washer component 11 and the retaining ring 18 of FIGS. 12 and 13 operate in the same manner as discussed above in connection with FIGS. 3 and 4.

Although the devices have been described in detail for the purpose of illustration based on what is currently considered to be the most practical and preferred embodiments, it is to be understood that such detail is solely for that purpose and that the systems and methods are not limited to the disclosed embodiments, but on the contrary, is intended to cover modifications and equivalent arrangements that are within the spirit and scope of the appended claims. For example, it is to be understood that the present systems and methods contemplate that, to the extent possible, one or more features of any embodiment can be combined with one or more features of any other embodiment.

The invention claimed is:

1. A medical injection device comprising:
- a housing having a distal end and a proximal end;
- a brake tower having a proximal end portion, a distal end portion, and a sidewall therebetween defining a longitudinal axis;
- a cartridge received within the housing distally of the brake tower and holding a composition therein, wherein a proximal end portion of the cartridge is configured to extend at least partially within the distal end portion of the brake tower along the longitudinal axis;
- a retaining ring positioned between the proximal end portion of the cartridge and the distal end portion of the brake tower, and
- a spring washer component, wherein the spring washer component is held within the distal end portion of the brake tower by the retaining ring, and wherein the retaining ring is secured to an interior surface of the distal end portion of the brake tower.

2. The medical injection device of claim 1, wherein the spring washer component is configured to bias the cartridge distally relative to the brake tower.

3. The medical injection device of claim 1, wherein the spring washer component and the retaining ring each have an opening formed therethrough, and wherein the respective openings are sized to allow a piston rod to extend therethrough.

4. The medical injection device of claim 1, wherein the retaining ring is a C-shaped ring.

5. The medical injection device of claim 1, wherein the retaining ring is secured within a groove formed within an interior sidewall surface of the brake tower.

6. The medical injection device of claim 1, wherein the retaining ring comprises a plurality of projections extending therefrom.

7. The medical injection device of claim 1, wherein the retaining ring is substantially convex.

8. A medical injection device comprising:
- a housing having a distal end and a proximal end;
- a brake tower having a proximal end portion, a distal end portion, and a sidewall therebetween defining a longitudinal axis;

a cartridge received within the housing distally of the brake tower and holding a composition therein, wherein a proximal end portion of the cartridge is configured to extend at least partially within the distal end portion of the brake tower along the longitudinal axis;

a cartridge housing received within the housing distally of the brake member and configured to hold the cartridge therein;

an injection needle at a distal end of the housing and in fluid communication with the cartridge;

an actuation member at a proximal end of the housing, the actuation member configured to actuate the medical injection device to deliver the composition through the injection needle;

a spring washer component, wherein the spring washer component is positioned within the distal end portion of the brake tower; and a retaining ring positioned between the proximal end portion of the cartridge and the distal end portion of the brake tower, wherein the retaining ring is secured to an interior surface of the distal end portion of the brake tower to hold the spring washer component within the distal end portion of the brake tower.

9. The medical injection device of claim 8, wherein the spring washer component is configured to bias the cartridge distally relative to the brake tower.

10. The medical injection device of claim 8, wherein the spring washer component and the retaining ring each have an opening formed therethrough, and wherein the respective openings are sized to allow a piston rod to extend therethrough.

11. The medical injection device of claim 8, wherein the spring washer component is a sinusoidal spring washer.

12. The medical injection device of claim 8, wherein the retaining ring is a C-shaped ring.

13. A medical injection device comprising:

a housing having a distal end and a proximal end;

a brake tower having a proximal end portion, a distal end portion, and a sidewall therebetween defining a longitudinal axis;

a cartridge received within the housing distally of the brake tower and holding a composition therein, wherein a proximal end portion of the cartridge is configured to extend at least partially within the distal end portion of the brake tower along the longitudinal axis;

a cartridge housing received within the housing distally of the brake member and configured to hold the cartridge therein;

an injection needle at a distal end of the housing and in fluid communication with the cartridge;

an actuation member at a proximal end of the housing, the actuation member configured to actuate the medical injection device to deliver the composition through the injection needle;

a retaining ring positioned between the proximal end portion of the cartridge and the distal end portion of the brake tower, wherein the retaining ring is press-fittingly secured to an interior surface of the distal end portion of the brake tower; and a spring washer component, wherein the spring washer component is held within the distal end portion of the brake tower by the retaining ring.

14. The medical injection device of claim 13, wherein the retaining ring comprises a plurality of projections extending therefrom.

15. The medical injection device of claim 13, wherein the retaining ring is substantially convex.

* * * * *